United States Patent
Heggie et al.

(10) Patent No.: US 11,059,021 B2
(45) Date of Patent: Jul. 13, 2021

(54) PROCESS FOR THE PREPARATION OF INTERMEDIATES USEFUL IN THE PREPARATION OF NON-IONIC CONTRAST AGENTS

(71) Applicant: Hovione Scientia Limited, Ringaskiddy (IE)

(72) Inventors: William Heggie, Palmela (PT); John Naber, Stow, MA (US); Patrick R. Bazinet, Sommerville, MA (US); Filipe Tomas, Robbinsville, NJ (US)

(73) Assignee: Hovione Scientia Limited, Ringaskiddy (IE)

( * ) Notice: Subject to any disclaimer, the term of this patent is extended or adjusted under 35 U.S.C. 154(b) by 0 days.

(21) Appl. No.: 15/578,952

(22) PCT Filed: Jun. 2, 2016

(86) PCT No.: PCT/GB2016/051633
§ 371 (c)(1),
(2) Date: Dec. 1, 2017

(87) PCT Pub. No.: WO2016/193740
PCT Pub. Date: Dec. 8, 2016

(65) Prior Publication Data
US 2018/0169607 A1 Jun. 21, 2018

(30) Foreign Application Priority Data
Jun. 2, 2015 (PT) .......................... 108524

(51) Int. Cl.
*B01J 19/18* (2006.01)
*C07C 227/04* (2006.01)
(Continued)

(52) U.S. Cl.
CPC ....... *B01J 19/1818* (2013.01); *B01J 19/0006* (2013.01); *B01J 19/0053* (2013.01);
(Continued)

(58) Field of Classification Search
None
See application file for complete search history.

(56) References Cited

U.S. PATENT DOCUMENTS

| 4,250,113 A * | 2/1981 | Nordal | ................. C07C 237/46 564/153 |
| 8,163,965 B2 | 4/2012 | Cervenka et al. | |

(Continued)

FOREIGN PATENT DOCUMENTS

| CN | 101248027 A | 2/2008 |
| CN | 101233092 A | 7/2008 |

(Continued)

OTHER PUBLICATIONS

Henkel ("Reactor Types and Their Industrial Applications" Ullmann's Encyclopedia of Industrial Chemistry, p. 293-327, first published Jun. 15, 2000, downloaded from https://doi.org/10.1002/14356007.b04_087 on Mar. 20, 2019) (Year: 2000).*

(Continued)

*Primary Examiner* — Amy C Bonaparte
(74) *Attorney, Agent, or Firm* — MacMillan, Sobanski & Todd, LLC

(57) ABSTRACT

The invention relates to a process for the preparation of one or more intermediate chemical compounds useful in the preparation of non-ionic contrast agents wherein the process is carried out continuously using one or more flow procedures.

27 Claims, 6 Drawing Sheets

(51) Int. Cl.
  *C07C 227/18* (2006.01)
  *C07C 231/02* (2006.01)
  *C07C 231/12* (2006.01)
  *C07C 227/16* (2006.01)
  *B01J 19/00* (2006.01)
  *C07C 17/12* (2006.01)
  *C07C 22/04* (2006.01)
  *C07C 229/62* (2006.01)
  *C07C 233/69* (2006.01)
  *C07C 237/46* (2006.01)

(52) U.S. Cl.
  CPC .............. *C07C 17/12* (2013.01); *C07C 22/04* (2013.01); *C07C 227/04* (2013.01); *C07C 227/16* (2013.01); *C07C 227/18* (2013.01); *C07C 229/62* (2013.01); *C07C 231/02* (2013.01); *C07C 231/12* (2013.01); *C07C 233/69* (2013.01); *C07C 237/46* (2013.01); *B01J 2219/0004* (2013.01); *B01J 2219/00033* (2013.01); *B01J 2219/00051* (2013.01); *B01J 2219/00162* (2013.01); *B01J 2219/00164* (2013.01); *B01J 2219/00182* (2013.01); *B01J 2219/00186* (2013.01)

(56) References Cited

U.S. PATENT DOCUMENTS

| | | | |
|---|---|---|---|
| 8,829,241 B2 | 9/2014 | Cervenka et al. | |
| 8,835,690 B2 | 9/2014 | Tjosas | |
| 9,403,757 B2 | 8/2016 | Haaland | |
| 2011/0021821 A1* | 1/2011 | Cervenka | C07C 231/02 564/153 |
| 2011/0021822 A1* | 1/2011 | Askildsen | C07C 231/12 564/153 |
| 2011/0021834 A1* | 1/2011 | Askildsen | C07C 231/24 564/156 |
| 2013/0338401 A1* | 12/2013 | Tjosas | B01J 19/0093 564/478 |

FOREIGN PATENT DOCUMENTS

| | | |
|---|---|---|
| CN | 103391918 A | 11/2013 |
| CN | 104768921 A | 7/2015 |
| EP | 2281804 A1 | 2/2011 |
| EP | 2281811 A1 | 2/2011 |
| EP | 2281814 A1 | 2/2011 |
| WO | 9824757 A1 | 6/1998 |
| WO | 2012108777 A1 | 8/2012 |

OTHER PUBLICATIONS

Merck Index entry for Iohexol, downloaded from https://www.rsc.org/Merck-Index/monograph/m6365/iohexol?q=authorize on Mar. 20, 2019 (Year: 2019).*

Webb ("Continuous flow multi-step organic synthesis" Chemical Science, 2010, p. 675-680) (Year: 2010).*

Sanz ("Continuous Flow Synthesis. A Pharma Perspective" Journal of Medicinal Chemistry, 2012, 55, p. 4062-4098) (Year: 2012).*

Hopkin ("A flow-based synthesis of Imatinib: the API of Gleevec" Cehm Commun. 2010, 46, p. 2450-2452) (Year: 2010).*

Ley ("ReactIR Flow Cell" Org. Process Res. Dev. 2010, 14, p. 393-404) (Year: 2010).*

Britton ("Multi-step continuous-flow synthesis" Chem. Soc. Rev. 2017, 46, p. 1250-1271) (Year: 2017).*

PCT International Search Report and Written Opinion, Application No. PCT/GB2016/051633, dated Sep. 1, 2016.

PCT International Preliminary Report on Patentability Chapter II, Application No. PCT/GB2016/051633, dated May 9, 2017.

PCT Receipt of Demand, Application No. PCT/G62016/051633, dated Jan. 10, 2017.

Australian Examination Report, Application No. 2016272537, dated Nov. 8, 2019.

Chinese First Office Action, Application No. 201680045292.8, dated Oct. 29, 2019.

Chinese Office Action, Application No. 201680045292.8, dated Jun. 5, 2020.

Israeli Office Action, Application No. 256044, dated Oct. 24, 2019.

Indian Office Action, Application No. 201717043408, dated Feb. 11, 2020.

* cited by examiner

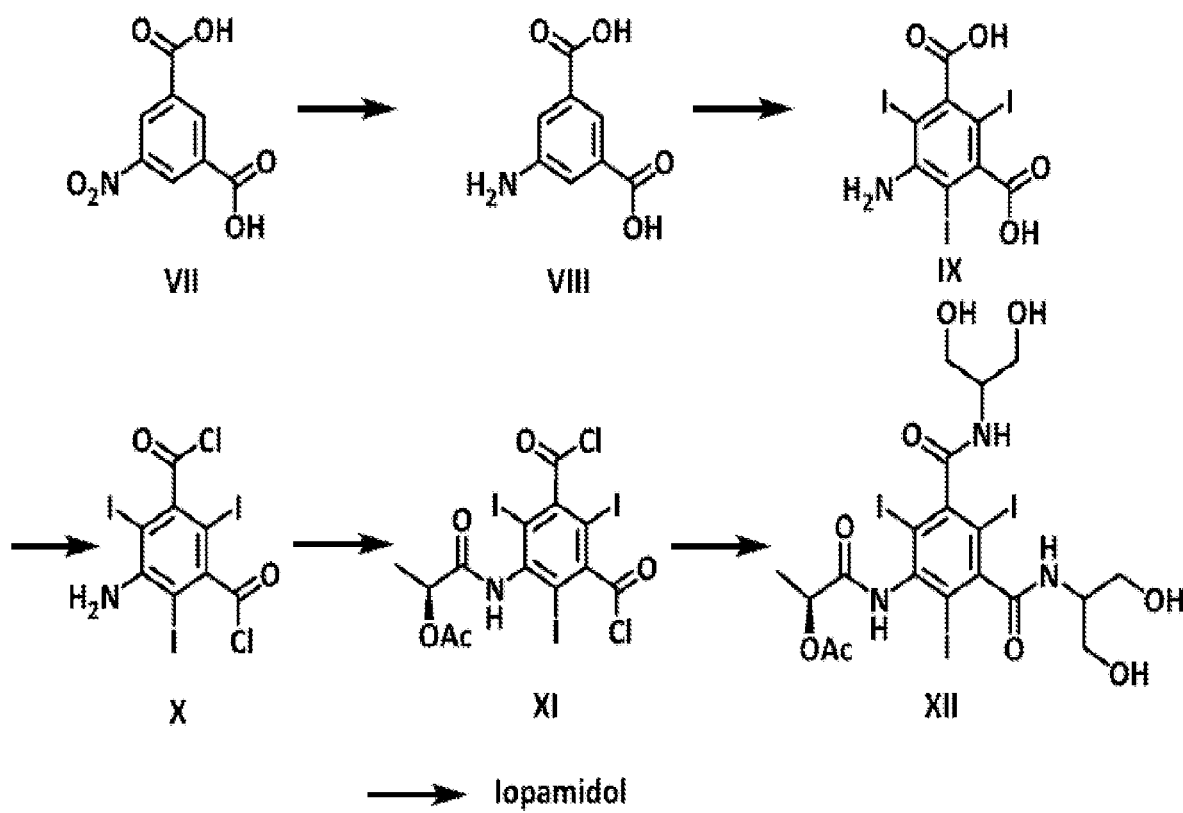
Figure 2: A synthesis sequence for the preparation of Iopamidol.

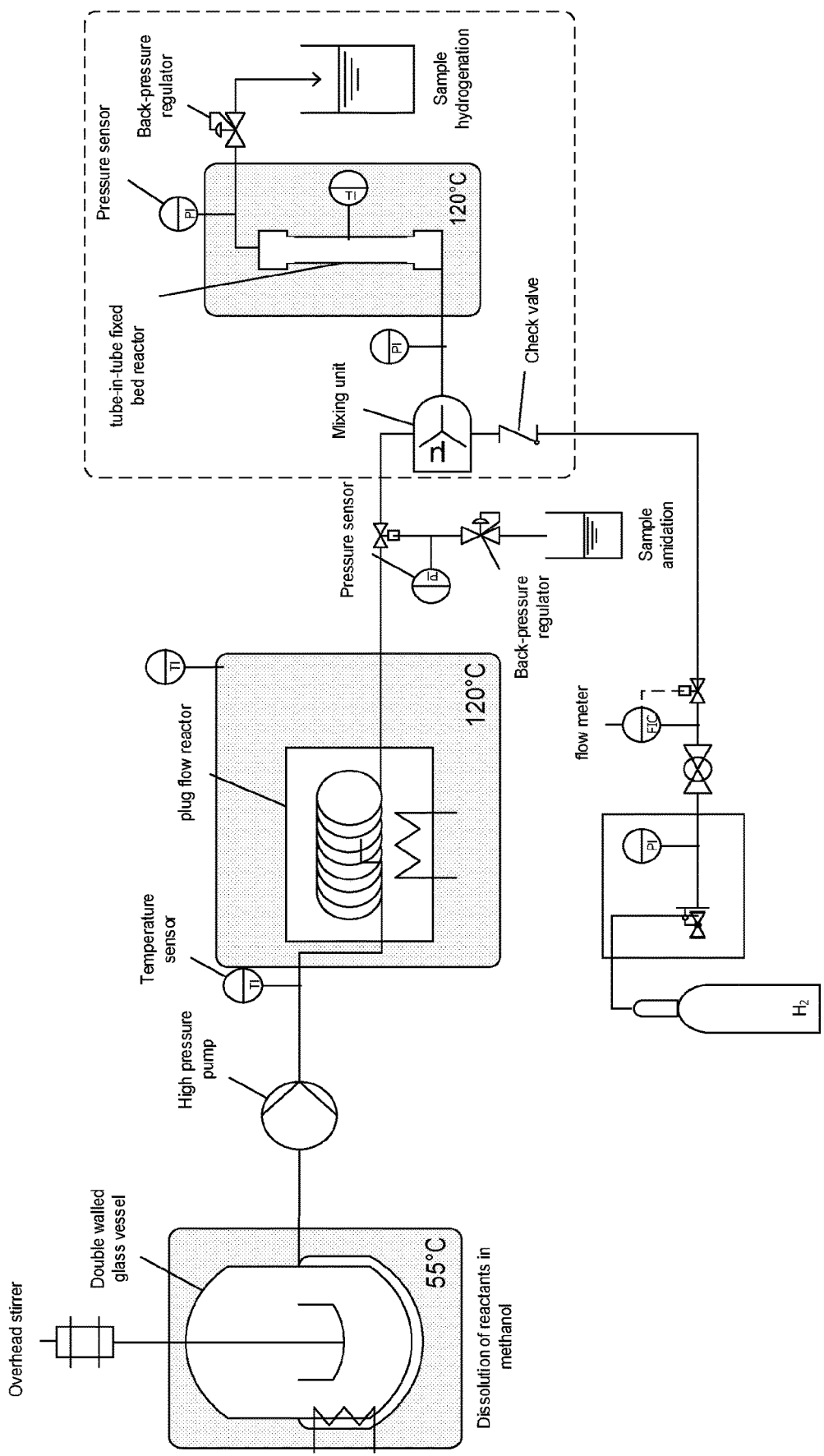
Figure 3: Schematic of an experimental set-up for amidation and hydrogenation (e.g. for part A of Example 1).

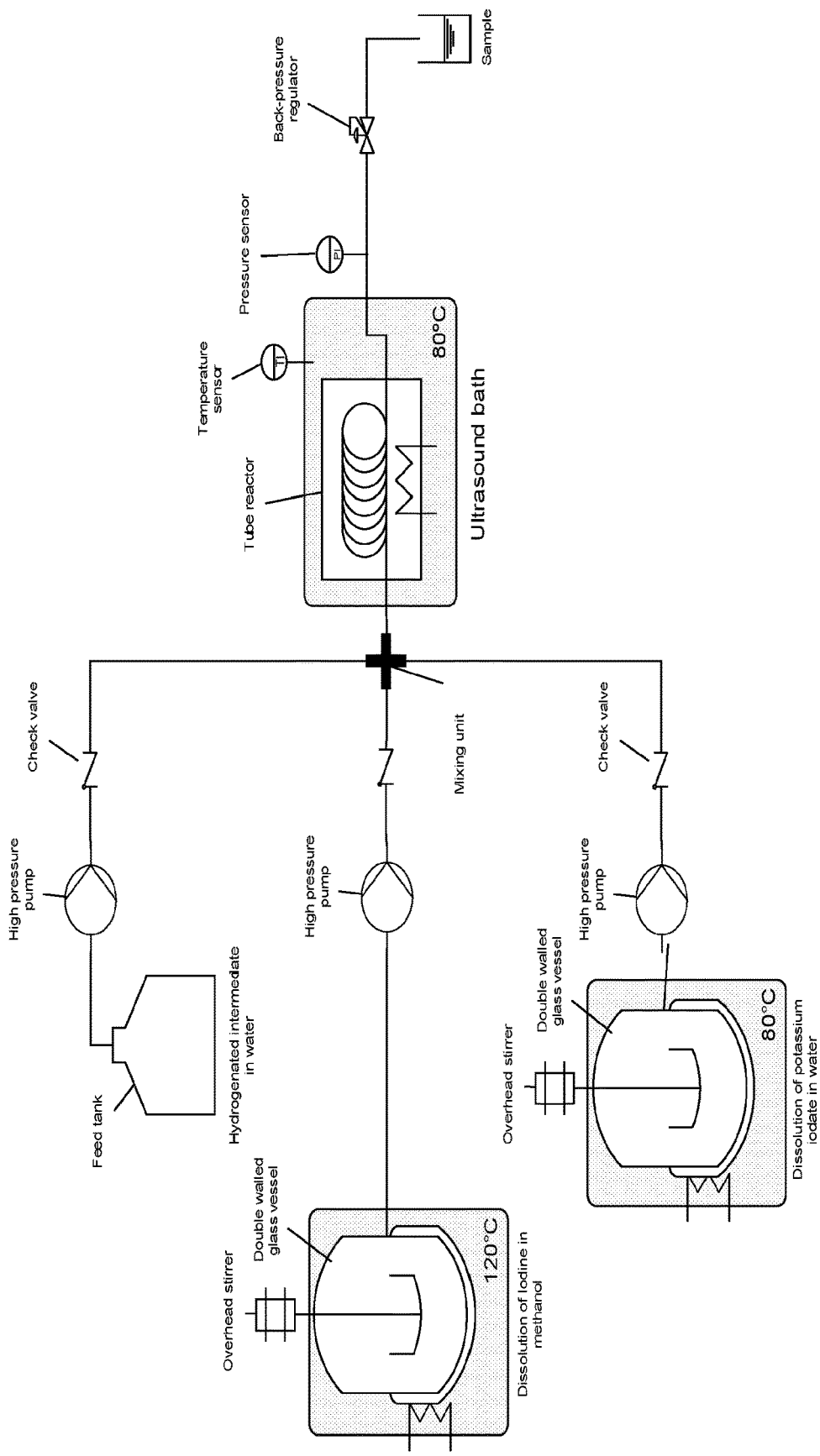
Figure 4: Schematic of an experimental set-up for iodination (e.g. for part B of Example 1).

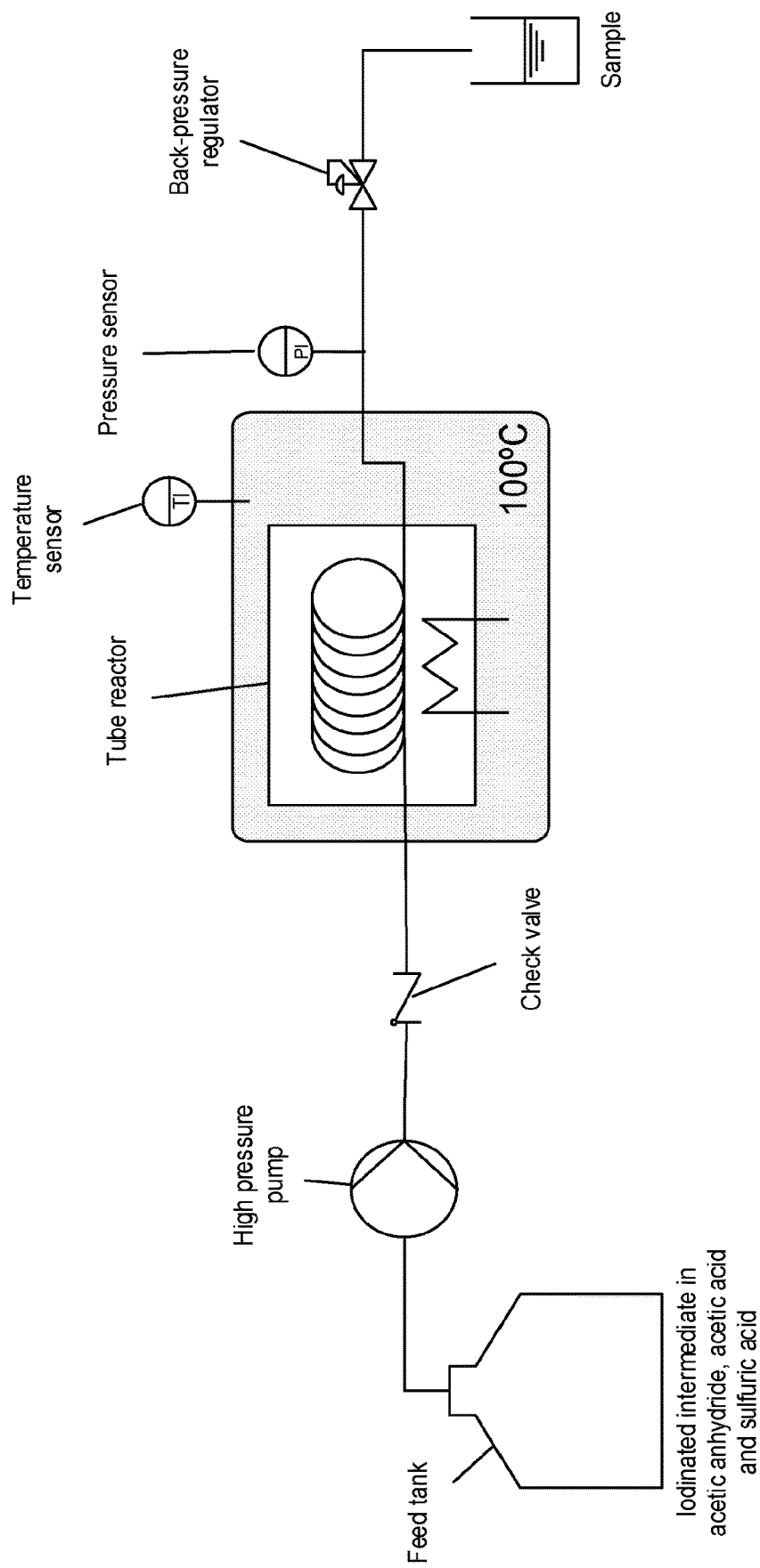
Figure 5: Schematic of an experimental set-up for acylation (e.g. for part C of Example 1).

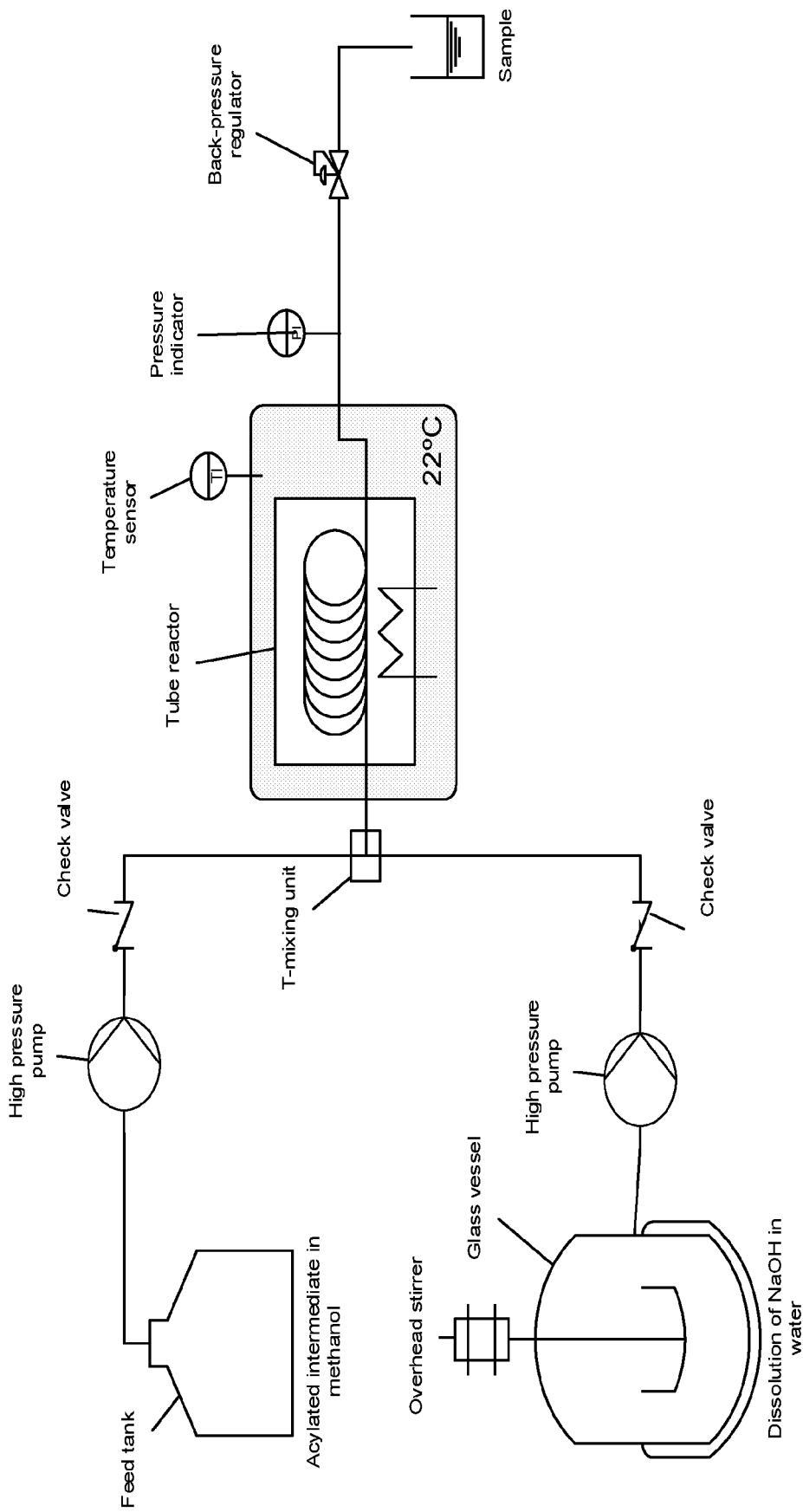
Figure 6: Schematic of an experimental set-up for hydrolysis (e.g. for part D of Example 1).

PROCESS FOR THE PREPARATION OF INTERMEDIATES USEFUL IN THE PREPARATION OF NON-IONIC CONTRAST AGENTS

The present invention claims the benefit of the PCT/GB2016/051633 filed Jun. 2, 2016, which claims priority to PT/108524 filed Jun. 2, 2015.

FIELD OF THE INVENTION

The present invention relates generally to the manufacture of intermediate chemical compounds which can be used for the production of non-ionic contrast agents. Specifically, the invention describes a process that allows the synthesis of said intermediate chemical compounds useful for the production of non-ionic contrast agents to be carried out continuously in one or more continuous flow reactors, which are of reduced dimensions in comparison with conventional stirred tank reactors (CSTRs), without the need to either isolate or purify any of the compounds produced at intermediary steps.

BACKGROUND OF THE INVENTION

Non-ionic contrast agents are produced in multi-ton quantities by the pharmaceutical industry. Typical non-ionic contrast agents comprise Iobitridol (EP 437144, U.S. Pat. No. 5,043,152), Iodixanol (EP 108638), Iohexol (DE 2726196, U.S. Pat. No. 4,250,113), Iomeprol (EP 026281, U.S. Pat. No. 4,352,788), Iopamidol (DE 2547789, U.S. Pat. No. 4,001,323), Iopentol (EP 105752), Iopromide (DE 2909439, U.S. Pat. No. 4,364,921), Iotrolan (EP 33426, U.S. Pat. No. 4,341,756), Ioversol (EP 83964, U.S. Pat. No. 4,396,598), Ioxilan (WO 8700757, U.S. Pat. No. 5,035,877). All have a 2,4,6-triodinated phenyl ring; and intermediates useful in their preparation can be produced by continuous processes according to the present invention. According to the present invention, it may also be possible to completely produce some non-ionic contrast agents via continuous processes. These non-ionic contrast agents are generally used in high doses in the clinic wherein a patient may be dosed at more than 100 g at a time. Therefore, the present inventors have recognized there is a need to have very efficient processes which are capable of producing material of very high quality which, in turn, minimizes the quantities of impurities that are given to the patient during each treatment. To reduce the cost of the final product, it is critical to optimize any synthetic process. Even a small improvement in reaction design can lead to significant savings in a large scale production. The present invention discloses continuous processes for use over a multi-step chemical synthesis to produce intermediate chemical compounds useful in the preparation of non-ionic contrast reagents.

European Patent Application EP 2281804 describes a process for the iodination of 5-amino-N,N'-bis(2,3-dihydroxypropyl-isophthalamide (ABA—compound of formula III of FIG. 1) or ABA-HCl to produce 5-amino-N,N'-bis(2,3-dihydroxypropyl)-2,4,6-triiodoisophthalamide (compound IV of FIG. 1) using CSTRs. This process involves the sequential transfer of the reactants from one vessel to another in a cascade sequence, with no indication of the velocity at which this is done or the retention time in each CSTR. Further, it will be appreciated that analysis of the excess amount of iodinating agent is required to ascertain the quantity of quenching reagent prior to the purifications steps, which also are carried out in CSTRs.

We have now found that it is possible to carry out continuous processes to synthesize intermediate chemical compounds useful in the preparation of non-ionic contrast agents using, in particular, one or more flow procedures.

SUMMARY OF THE INVENTION

According to the present invention, there is provided a process for the preparation of one or more intermediate chemical compounds useful in the preparation of non-ionic contrast agents wherein the process is carried out continuously using one or more flow procedures.

DESCRIPTION OF THE FIGURES

FIG. 2: A synthesis sequence for the preparation of Iopamidol.

FIG. 3: Schematic of an experimental set-up for amidation and hydrogenation (e.g. for part A of example 1).

FIG. 4: Schematic of an experimental set-up for iodination (e.g. for part B of example 1).

FIG. 5: Schematic of an experimental set-up for acylation (e.g. for part C of example 1).

FIG. 6: Schematic of an experimental set-up for hydrolysis (e.g. for part D of example 1).

DETAILED DESCRIPTION OF THE INVENTION

Figure 1:
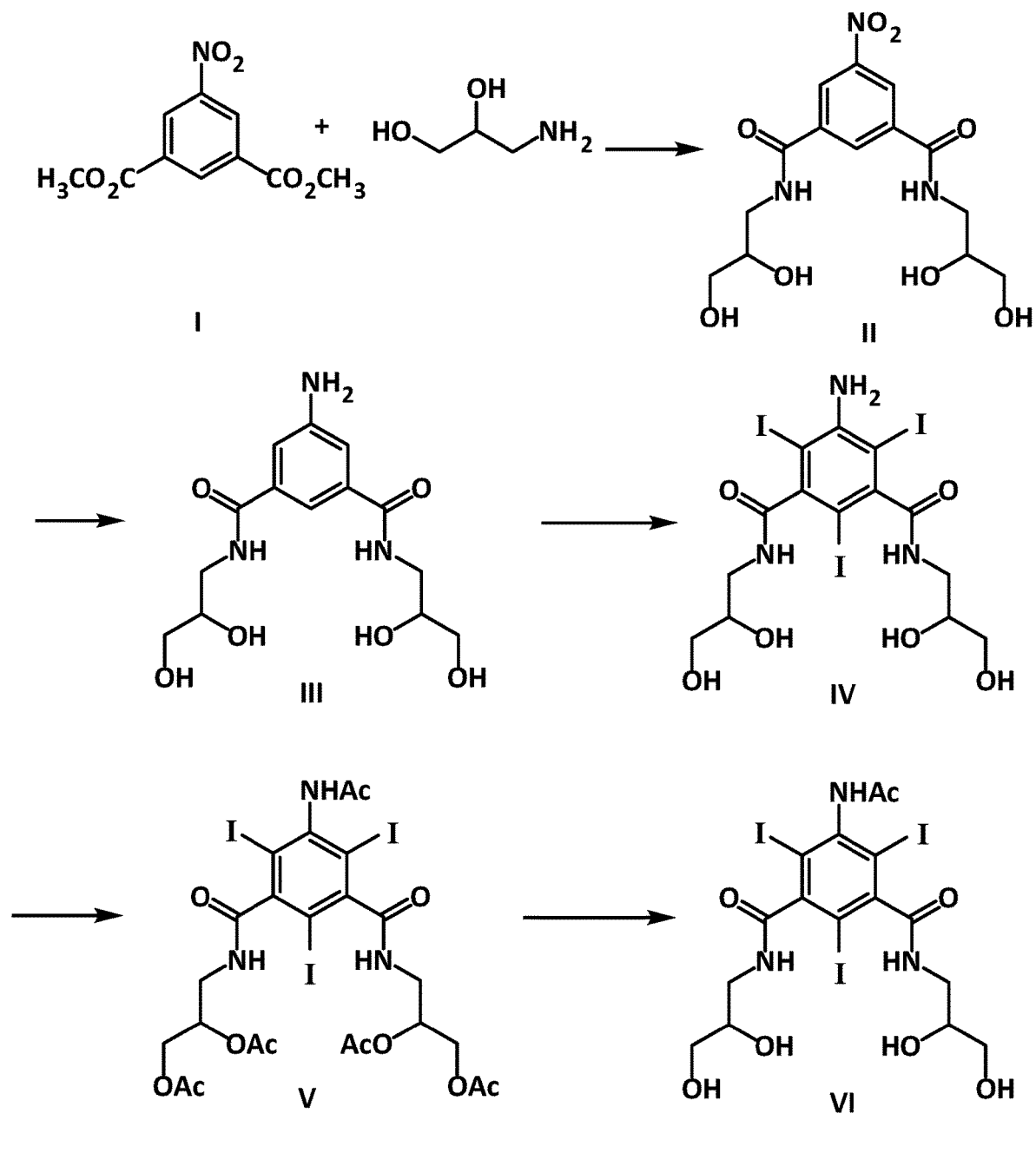
FIG. 1: A synthesis sequence for the preparation of Iohexol.

The term "intermediate chemical compounds useful in the preparation of non-ionic contrast agents" as used herein refers to a chemical compound which may undergo further synthetic reaction(s) to produce a non-ionic contrast agent including, but not limited to, Iobitridol, Iodixanol, Iohexol, Iomeprol, Iopamidol, Iopentol, Iopromide, Iotrolan, Ioversol and Ioxilan. The term "intermediate chemical compounds useful in the preparation of non-ionic contrast agents" is not intended to include reagents which do not undergo further reactions that assist in the synthetic process for preparing non-ionic contrast agents nor those reagents which undergo reactions that do not lead to the production of a non-ionic contrast agent. More specifically, the term is not intended to cover reagents that partake in side reactions. The intermediate chemical compounds useful in the preparation of non-ionic contrast agents may, for example, include the chemical intermediate compounds of a multi-step chemical synthesis sequence for the preparation of a non-ionic contrast agent. Preferably, intermediate chemical compounds useful in the preparation of non-ionic contrast agents comprise any of the compounds of formulae I, II, III, IV, V and/or VI as shown in FIG. 1 (FIG. 1). More preferably, the intermediate chemical compounds useful in the preparation of non-ionic contrast agents comprise the compounds of formulae III, IV, V and/or VI. Also, preferably, intermediate chemical compounds useful in the preparation of non-ionic contrast agents comprise any of the compounds of formulae VII, VIII, IX, X, XI and/or XII as shown in FIG. 2 (FIG. 2). More preferably, the intermediate chemical compounds useful in the preparation of non-ionic contrast agents comprise the compound of formulae IX, X, XI and/or XII.

The process for the preparation of the intermediate chemical compounds useful in the preparation of non-ionic contrast agents as according to the present invention will comprise using one or more flow procedures to carry out a continuous process.

The term "flow procedures" as used herein relates to those procedures, for example, the use of certain apparatus and/or certain conditions, necessary to enable the continuous running of chemical synthesis. Flow procedures, as used herein, does not encompass a traditional batch process. Preferably, a continuous reactor is used to carry material as a flowing stream, as will be understood by those skilled in this field.

A process may be defined as continuous in that it is characterized by continuous feeding of the reactants to the reactor with continuous formation and exiting of a product stream. The presently disclosed continuous process may be further described as set out below.

A continuous process according to the present invention may be advantageous for a number of reasons including, but not limited to, improved purity and yield of the product and reduced effluent; thus, making the present process more environmentally friendly.

The term "continuous flow reactor" is used to refer to those reactors which enable chemical reactions to occur in a continuous flow. Continuous flow reactors may also be known as continuous tubular reactors. The continuous flow reactor may comprise a pipe reactor, a plug flow reactor, a tube reactor or another commercially available continuous flow reactor, or a combination of two or more such reactors. Continuous flow reactors occupy considerably less volume than CSTRs Continuous flow reactors can be made of any suitable compatible material, for example, comprising glass, Hastalloy®, silicon carbide, stainless steel and/or one or more high performance alloys. Any commercially available flow reactors may be used for the process, especially those having an inbuilt capability to cause turbulence along the direction of flow. The continuous flow reactors may comprise static mixing apparatus. A continuous flow reactor may handle slurries, be subjected to a particular temperature or temperature range and/or be subjected to a certain pressure or pressure range. Where more than one continuous flow reactor or a single continuous flow reactor comprising a combination of the reactors listed above is used, the continuous flow reactors/reactors may be connected to one another such that fluid communication is possible. With respect to the term "connected", as used herein, it should be understood that the continuous flow reactors/reactors need not be attached directly to one another, but rather that the continuous flow reactors/reactors should be in fluid communication with each other. If desired, the reactors may be in direct contact. That is to say that they may be connected directly to one another, such that fluid communication is possible between their bores.

The continuous process for preparing intermediate chemical compounds useful in the preparation of non-ionic contrast agents may comprise a multi-step chemical synthesis comprising two or more sequential reactions, each reaction leading to the production of an intermediate chemical compound useful in the preparation of non-ionic contrast agents. The term "multi-step chemical synthesis" as used herein generally relates to a synthetic process comprising multiple chemical reactions. The term is not intended to cover a synthesis wherein merely one chemical reaction may be done over multiple steps. One or more reactions of the process may be carried out in one or more continuous flow reactors. All the reactions may be carried out in one or more continuous flow reactors. Each reaction may be carried out in a separate continuous flow reactor. Any intermediate chemical compound resulting from the process may be used to prepare a non-ionic contrast agent.

The process may comprise preparing at least two intermediate chemical compounds useful in the preparation of non-ionic contrast agents in sequence. The process may comprise at least two chemical reaction steps carried out continuously one after the other. Further, the product of the first chemical reaction step may be a first intermediate that is used as a reactant of the second chemical reaction step to produce a second intermediate compound, this being repeated in the same way for any subsequent reaction steps. The process is preferably carried out without isolation or purification of any intermediate chemical compound, although isolation and/or purification of one or more intermediate compounds may be done if desired, and in particular where the intermediate chemical compound that results from the process (i.e. is the final product of the process) is the desired final intermediate chemical compound useful in the preparation of non-ionic contrast agents, then this compound may be isolated if desired. Alternatively, where possible (from a synthetic chemical point of view) the continuous process may be continued right up until production of the non-ionic contrast agent itself.

The process may comprise at least two chemical reactions which are carried out consecutively, without interruption; such interruptions may comprise an isolation or purification step. If desired, the process may include one or more additional steps. The additional steps may for example comprise one or more washing steps, one or more purification steps, one or more isolation steps, one or more solvent modification steps, one or more solvent switching steps or combinations thereof.

The conditions within the one or more continuous flow reactors may be controlled. This may be done, for example, to enable a particular chemical or physical reaction to occur or obtain a desired reaction rate. Controlling the conditions of the one or more continuous flow reactors may comprise adjusting or altering one or more of the following: the temperature within one or more continuous flow reactors, the pressure within one or more continuous flow reactors, the solvents or solvent systems within one or more flow reactors, flow rates within one or more continuous flow reactors and the concentration of reactant within the feed entering one or more continuous flow reactors. Any combinations of the aforementioned properties or parameters may be controlled in one or more continuous flow reactors. Any combinations of the aforementioned properties or parameters may be controlled in all the continuous flow reactor(s).

The flow rate of reagents through the one or more continuous flow reactors may be controlled, altered or adjusted depending on the chemical reaction to be carried out. The flow rate of reagents may be different along one or more selected distances of the one or more continuous flow reactors, optionally the one or more selected distances may not overlap. That is to say that the flow rate of reagents may differ from within sections of the one or more continuous flow reactors. The flow rate of reagents associated with a reaction step may affect the flow rate associated with the subsequent reaction step. Reagents may travel along a selected distance of the continuous flow reactor at different flow rates. The flow rates of reagents through the one or more continuous flow reactor may be controlled, adjusted or altered using pumps, adjacent flow meters and control valves. A change in flow rate may be carried out using one or more holding tank. As an illustrative example, consider a first reaction (laboratory scale) with a flow rate of 10 mL/min and a second reaction with a flow rate of 5 mL/min, the holding tank may be installed in between the reaction steps (or more specifically continuous flow reactors or reactors), whilst reaction one is feeding the holding tank at 10 mL/min a second pump may pump the resulting feed from reaction one from the holding tank at a slower flow rate of 5 mL/min. It will be understood that in such circumstances the holding tank does not stop the continuous process, just serve as a buffer to modulate flow rates between two reactions (or more specifically continuous flow reactors or reactors).

The flow rate values and flow rate ranges described herein may be suitable for a particular apparatus set-up; therefore, the corresponding flux values/ranges (in litres per area per hour) may used instead to generalize the flow of reagents for apparatus of any size/dimensions. As such the terms flux and flow rate may be used interchangeably herein.

The flux of reagents along a selected distance of the continuous flow reactor, or the flux which is associated with an amidation reaction may for example be about 1,000-2,000, such as 1,039-1,906, litres per meter squared per hour (Litres/m$^2$/hour). The yield of an amidation reaction may preferably be about (range) 95% or more. The flux of some reagents (i.e. hydrogen) along a selected distance of the continuous flow reactor or the flux (of reagents) which is associated with a hydrogenation reaction may for example be about 80,000-110,000, such as 81,803-105,863, litres per meter squared per hour (Litres/m$^2$/hour). The flux of reagents along a selected distance of the continuous flow reactor or the flux (of reagents) which is associated with an iodination reaction may for example be 3,000-19,000 such as 3,056-18,335, litres per meter squared per hour (Litres/m$^2$/hour). The yield of an iodination reaction may for example be at least about 85%. The flux of reagents along a selected distance of the continuous flow reactor or the flux (of reagents) which is associated with an acylation reaction may for example be 3,000-19,000 such as 3,056-18,335, litres per meter squared per hour (Litres/m$^2$/hour). The yield of an acylation reaction may for example be at least about 74%. The flux of reagents along a selected distance of the continuous flow reactor or the flux (of reagents) which is associated with a hydrolysis reaction may for example be 3,000-7,000 such as 3,056-6,112, litres per meter squared per hour (Litres/m$^2$/hour). The yield of a hydrolysis reaction may for example be at least about 97%.

The process may comprise one or more of the following chemical reactions: (i) nucleophilic acyl substitution, (ii) reduction of a nitro group, (iii) Halogenation, (iv) acylation, (v) esterification and (vi) hydrolysis.

Further the nucleophilic acyl substitution may comprise one or more of: (a) substitution of an alcohol functional group for a halide; (b) substitution of a halide for an amine functional group; and (c) amidation. The reduction of a nitro group may comprise hydrogenation of the nitro group. The halogenation may comprise iodination. The hydrolysis may comprise selective hydrolysis. Such selective hydrolysis may comprise only hydrolyzing a particular functional group of the reactant compound. Such selective hydrolysis may occur, during certain reaction conditions, due to the inherent reactivity of certain functional groups over others, due to the use of a protecting group, due to activation of a functional group or by any other suitable means.

Each reaction may be carried out in a heterogeneous or homogeneous environment. The one or more continuous flow reactors may be adapted to carry out reactions in a heterogeneous and/or homogeneous environment. In particular, one or more continuous flow reactors of may be adapted to carry out heterogeneous and/or homogeneous reactions. For example, the continuous flow reactors may comprise therein (e.g. within their bores of the reactor) one or more catalysts. The catalysts may be homogenous or heterogeneous with respect to the reactants, reagents and/or solvents.

The process may comprise a multi-step chemical synthesis which:
(i) produces any of the compounds of formula III, IV, V and/or VI, depicted in FIG. 1; or
(ii) produces any of the compounds of formula IX, X, XI, XII, and/or Iopamidol depicted in FIG. 2; or
(iii) produces Iodixanol.

The process may comprise the following series of chemical reactions:
(i) amidation, reduction of a nitro group via hydrogenation, iodination, acylation and selective hydrolysis; or
(ii) reduction of a nitro group via hydrogenation, iodination, nucleophilic acyl substitution and acylation.

The intermediate chemical compound is most preferably 5-acetamido-N1,N3-bis(1,3-dihydroxypropan-2-yl)-2,4,6-triiodoisophthalamide (the compound of formula VI) or the compound of formula XII. The intermediate chemical compound useful in the preparation of non-ionic contrast agents may be further reacted to prepare any of the non-ionic contrast agents Iohexol, Iodixanol or Iopamidol. Preferably the non-ionic contrast agent is Iohexol, Iodixanol or Iopamidol.

Preferably, the non-ionic contrast agent is Iohexol or Iodixanol and the intermediate chemical compounds useful in the preparation of the non-ionic contrast agent are the compounds of formulae II, III, IV, V and/or VI as depicted in FIG. 1. Most preferably, the intermediate chemical compound useful in the preparation of the non-ionic contrast agent is compound VI depicted in FIG. 1. Preferably, the non-ionic contrast agent is Iopamidol and the intermediate chemical compounds useful in the preparation of the non-ionic contrast agent are the compounds of formulae VIII, IX, X, XI and/or XII as depicted in FIG. 2. More preferably, the intermediate compound useful in the preparation of the non-ionic contrast agent is compound XII depicted in FIG. 2.

The process may or may not require the use of conventional stirred tank reactors (CSTRs) or other holding tanks, which may be used as described above.

Additionally, it has been found that at the output of each reactor, the purity, with regards to related compounds, of each intermediate is high, i.e. higher than 80%, preferably higher than 90% most preferably even reaching 100%, thus avoiding the build-up of impurities which could be detrimental to the subsequent reaction.

We have found, for example, that it is possible to carry out the whole of the sequence of synthetic reactions required to produce the compound of formula VI (depicted in FIG. 1), starting from compound of formula I (depicted in FIG. 1) without the need to isolate or purify any of the intermediate compounds of formulae II, III, IV and/or V. It is also possible to carry out the whole of the sequence of synthetic reactions required to produce the compound of formula XII, (depicted in FIG. 2), starting from compound of formula VII (depicted in FIG. 2), without the need to isolate or purify any of the intermediate compounds of formulae VIII, IX X and/or XI.

Referring to FIG. 1, Iohexol is an example of a non-ionic contrast agent. It may be produced by the synthetic sequence shown in FIG. 1. A key intermediate reactant useful in the production of Iohexol is 5-acetamido-N$^1$,N$^3$-bis(1,3-dihydroxypropan-2-yl)-2,4,6-triiodoisophthalamide (the compound of formula VI, in FIG. 1). Iohexol may be prepared by alkylation—for example, with chloropropan-1,2-diol—of the compound of formula VI. The presently claimed process may be suitable for the preparation of the compound of formula VI. The process is continuous over a multi-step chemical synthesis. The process may comprise a multi-step chemical synthesis which produces the intermediates displayed in the synthetic sequence in FIG. 1. The process may begin with 5 nitro-isophthalic acid dimethyl ester, the compound of formula I, which through amidation with isoserinol, produces the compound of formula II. This may be followed by reduction of the nitro group of the compound of formula II to an aromatic amino group to produce the compound of formula III. This may be followed by iodination of the compound of formula III to produce the triiodinated compound of formula IV. The compound of formula IV may, in turn, undergo acylation to give the acetamide and/or tetra-acetate ester, as depicted by the compound of formula V, and finally, the compound of formula V may undergo selective hydrolysis (e.g. of the four acetate ester groups) to give the intermediate of compound VI, which may be useful in the preparation of non-ionic contrast agents, such as Iohexol. Intermediate VI is also useful in the manufacture of Iodixanol, a dimeric non-ionic contrast agent. The above multi-step chemical synthesis is also suitable for the preparation of intermediate chemical compounds useful in the preparation of other non-ionic contrast agents, such as Iopamidol. As such the presently claim process is suitable for the preparation of intermediate chemical compounds useful in the preparation of other non-ionic contrast agents, such as Iopamidol. Schematics showing exemplary set-ups for carrying out reactions (discussed herein) according to the present invention are found in FIGS. 3 to 6.

It is possible, according to the present invention, to carry out the whole of the synthetic sequence, depicted in FIG. 1, from compound I to compound VI, without the use of CSTRs and/or without the need to isolate or purify any of the intermediate compounds II, III, IV and/or V. Of course, for convenience, the process may contain additional steps carried out before, during or after a reaction of said multi-step chemical synthesis. These additional steps are carried out so as to ensure that the process as defined herein remains continuous as also described herein. That is to say that the process remains continuous over the whole multi-step chemical synthesis. The additional steps may comprise purifying or isolating steps.

Other intermediate chemical compounds useful for the preparation of non-ionic contrast agent, such as the compound of formula XII, FIG. 2 may also be prepared by the presently claimed process. The compound of formula XII is used as an intermediate in the manufacture of Iopamidol, another non-ionic contrast agent. The compound of formula XII may be produced via other multi-step chemical synthesis than that described above.

The chemical synthesis for the preparation of the compound of formula XII may be suitable for the presently claim invention. Such, a process may comprise a multi-step chemical synthesis which produces the intermediates displayed in the sequence in FIG. 2. The process may begin with the reduction of a nitro group of the compound of formula VII to form the aromatic amine of the compound of formula VIII. This may be followed by the iodination of the compound of formula VIII to form the compound of formula IX. The compound of formula IX may undergo activation of the dicarboxylic acids, via a nucleophilic acyl substitution, to produce the compound of formula X. The compound of formula X may undergo amidation or two sequential amidation reactions to give the compound of formula XI or the intermediate reactant compound of formula XII, respectively. Alternatively, a similar sequence as that described above for the preparation of the compound of formula VI may be employed for the preparation of the compound of formula XII or Iopamidol.

It is, of course, possible, according to the present invention, to carry out the whole of the synthetic sequence from the compound of formula VII to the compound of formula XII without the use of CSTRs and/or without the need to isolate or purify any of the intermediate chemical compounds VIII, IX, X, XI and/or XII. For industrial applications this is particularly relevant as investment in CSTRs can be high and the plant fingerprint to house such equipment is also quite large. Of course, for convenience, the flow procedure may contain additional steps carried out before, during or after a reaction of said multi-step chemical synthesis. These additional steps are carried out so as to ensure that the process as defined herein remains continuous as defined herein. That is to say that the process remains continuous over the whole multi-step chemical synthesis. The additional steps may comprise purifying or isolating steps.

As mentioned above, an advantage of running this continuous process in continuous flow reactors, such as pipe reactors, is that the volume of solvents are considerably reduced in comparison with those used in CSTRs. This in turn leads to a subsequent reduction in effluent, thus making these processes more environmentally friendly.

The solvents used in the process may be common organic solvents, aqueous solvents, aqueous based solvents, water or mixtures thereof. Any compatible solvent or solvent system can be used. The solvent systems used may comprise colloidal suspensions or emulsions. The solvent systems used may comprise methanol, water or a mixture of both. The solvent systems may comprise mixtures of water-miscible organic solvents and water. They may also comprise water immiscible organic solvents in contact with or not in contact with water. Any specific combinations of the above listed solvents may be used. All of the reactions may not be optimally carried out in the same solvent or solvent system and when, and if necessary, adjustment of the solvent/solvent composition or a solvent switch may be carried out in a continuous manner—for example, without the need to isolate or purify intermediates.

The reaction rate of each individual reaction step, the flux/flow rate through each of the pipe reactors and the rate of solvent modification, the temperature and pressure can be adjusted so that flow through the whole of the multi-step chemical synthesis process does not require the use of holding tanks at intermediates stages. Although, as explained above, under certain circumstances, holding tanks may be utilized, but only in such a manner that their use does not greatly impact on the efficiency of the process as a whole, for example as described above. The output of the one or more continuous flow reactors is judiciously controlled in such a way that composition with regards to the intermediate, reactants, impurities and solvents etc. is suitable to be fed into the subsequent stage to allow for optimal reaction conditions.

Additionally, it has been found that at the output of each reactor the purity, with regards to related compounds, of each intermediate is high, i.e. higher than 80%, preferably higher than 90% most preferably even reaching 100%, thus avoiding the build-up of impurities which could be detrimental to the subsequent reaction.

The conditions in the continuous flow reactors may vary over a wide range. In particular, the conditions may vary from homogeneous reaction conditions to heterogeneous conditions. For example, a heterogeneous reaction may be utilized in the reduction of the nitro group reaction. In the case of the reaction where the nitro group is reduced (e.g. from the compound of formula II to produce the aromatic amine of the compound of formula III) the continuous flow reactor, which may be a pipe reactor, may be filled with a heterogeneous catalyst. The heterogeneous catalyst may, for example be palladium on carbon when the reaction is the hydrogenation of a nitro group.

Some reactions within the multi-step chemical synthesis may be carried out in a two-solvent system. For example, the acylation and hydrolysis steps, carried out for example to produce the compounds of formula V and VI, respectively, may be carried out in a two solvent system. Also continuous solvent extraction/wash steps may be applied to remove impurities, excess reagents or other undesirable materials which could be detrimental to subsequent chemical reactions or to the purity of the final product. The pressure in each of the reactors may be atmospheric or above atmospheric pressure and temperatures can vary from ambient to above 100° C. Of course, in certain circumstances it may be required to adjust the temperature to below ambient or even below 0° C.

Purification, isolation and drying of the final product, when this is so desired, can also be carried out in a continuous fashion using continuous crystallization, filtration and drying processes.

The examples described below are taken from of laboratory/pilot scale experiments. It will therefore be appreciated that the values and ranges discussed may be scaled up for commercial purposes.

The flow rates given below relate to the flow of reagent(s) along a selected distance of the continuous flow reactor, or a flow rate (of reagents) which is associated with a particular reaction described herein (i.e. amidation, hydrogenation, iodination, acylation or hydrolysis).

EXAMPLE 1

Part A: Continuous Amidation and Hydrogenation (Refer to FIG. 3 for Example Apparatus Set-Up)

Compound I and 1-aminopropanediol were dissolved in methanol (molar ratio 1:2.6:34). The solution was pumped through a plug flow reactor (diameter 2.1 cm, length 50 cm, set at 120° C. and 7.5 bar) with a flow rate of 9 mL min-1. HPLC at line indicated a yield of about 95%. Thereafter, the solution was passed through a t-unit where it is mixed with a hydrogen stream flowing at 183 mL min-1, before entering a tube-in-tube fixed bed column reactor (stainless steel, int. diameter 1.026 cm, length 80 cm, set at 120° C. and 10 bar) packed with 0.5% Pd (palladium) on an inert support. On exiting the pipe reactor, the excess hydrogen is removed from the liquid stream by a gas-liquid separator.

Listed below are ranges of parameters/variables which are suitable for carrying out Part A (continuous amidation and hydrogenation) in laboratory/pilot scale the ranges may of course be scaled up, as necessary, for commercial purposes.
  Molar ratio of compound I to 1-aminopropanediol: from 1:2 to 1:3
  Molar ratio of compound I to methanol: from 1:30 to 1:50
  Amidation temperature: from 100 to 130° C.
  Amidation pressure: from 2 to 10 bar
  Flow rate for amidation: from 6 to 11 mL min-1
  Flow rate of hydrogen: from 170 to 220 mL min-1
  Hydrogenation temperature: from 100 to 130° C.
  Hydrogenation pressure: from 5 to 20 bar Part B: Continuous Iodination (Refer to FIG. 4 for Example Apparatus Set-Up)

The stream from part a is diluted with water (ratio 1:3) to give feed A.

Feed B is prepared by dissolving iodine in methanol (molar ratio 1:45) and feed C is prepared by dissolving potassium iodate and sulfuric acid is water (molar ratio 1:0.25:45). Feeds A, B and C are mixed continuously in a ratio of 1:1.5:0.6, respectively, and pumped through a pipe reactor (internal diameter 0.5 cm, length 150 cm, set at 80° C. and 8 bar) in an ultrasonic bath, at a flow rate of 3 mL min-1. HPLC at line indicated a yield of 85% at the end of the pipe reactor.

Listed below are ranges of parameters/variables which are suitable for carrying out Part B (continuous iodination) in laboratory/pilot scale, the ranges may of course be scaled up, as necessary, for commercial purposes.
  Molar ratio of iodine to methanol: from 1:30 to 1:50
  Molar ratio of potassium iodate to sulfuric acid: from 1:0.1 to 1:1
  Molar ratio of potassium iodate to water: from 1:30 to 1:50
  Feed ratio of feed A to feed B: from 1:1.1 to 1:10
  Feed ratio of feed A to feed C: from 1:0.5 to 1:1.5
  Temperature: from 60 to 140° C.
  Pressure: from 5 to 15 bar
  Flow rate: from 1 to 6 mL min-1

Part C: Continuous Acylation (Refer to FIG. 5 for Example Apparatus Set-Up)

A solvent exchange was performed to the stream from part b, to give a solution of compound IV in acetic anhydride, acetic acid and sulfuric acid (molar ratio 1:20:62:0.1). The mixture was pumped through a tube reactor (internal diameter 0.05 cm, length 150 cm, set at 100° C. and 1.4 bar) with a flow rate of 2.95 mL min-1. HPLC at line gave a yield of 74%.

Listed below are ranges of parameters/variables which are suitable for carrying out Part C (continuous acylation) in laboratory/pilot scale, the ranges may of course be scaled up, as necessary, for commercial purposes.
  Molar ratio of compound IV to acetic anhydride: from 1:6 to 1:25
  Molar ratio of compound IV to acetic acid: from 1:50 to 1:80
  Molar ratio of compound IV to sulfuric acid: from 1:0.05 to 1:1
  Temperature: from 80 to 130° C.
  Pressure: from 2 to 10 bar
  Flow rate: from 0.01 to 0.06 mL min-1

Part D: Continuous Hydrolysis (Refer to FIG. 6 for Example Apparatus Set-Up)

A solvent exchange was performed to the stream from part c, to give feed D as a solution of compound V in methanol (molar ratio 1:125). Feed E is prepared by dissolving sodium hydroxide in water (molar ratio 1:27). Feeds D and E were mixed continuously in a t-unit (ratio of 1:1) and pumped through a pipe reactor (internal diameter 0.05 cm, length 100 cm, set at room temperature and pressure) with a flow rate of 0.05 mL min-1. HPLC at line indicated a yield of 97% at the end of the pipe reactor.

Listed below are ranges of parameters/variables which are suitable for carrying out Part D (continuous hydrolysis) in laboratory/pilot scale, the ranges may of course be scaled up, as necessary, for commercial purposes.
  Molar ratio of compound V to methanol: from 1:100 to 1:150

Molar ratio of Sodium hydroxide to water: from 1:25 to 1:50
Feed ratio of feed D to feed E: from 1:0.5 to 1:2
Temperature: from 22 to 75° C.
Pressure: from 1 to 10 bar
Flow rate: from 0.01 to 0.2 mL min-1

The invention claimed is:

1. A process for the preparation of two or more intermediate chemical compounds useful in the preparation of one or more non-ionic contrast agents, comprising
conducting a multi-step chemical synthesis comprising two or more sequential chemical reactions,
each sequential chemical reaction leading to the production of at least one of the two or more intermediate chemical compounds;
the two or more sequential reactions being carried out in one or more continuous flow reactors, wherein at least two of the two or more sequential reactions are carried out consecutively without interruption;
wherein the two or more sequential chemical reactions are selected from either set (i) of sequential steps, or set (ii) of sequential steps, as follows:
(i) sequential steps:
i-a) amidation,
i-b) reduction of a nitro group via hydrogenation,
i-c) iodination,
i-d) acylation, and
i-e) selective hydrolysis;
or
(ii) sequential steps:
ii-a) reduction of a nitro group via hydrogenation,
ii-b) iodination,
ii-c) nucleophilic acyl substitution, and
ii-d) acylation;
wherein the non-ionic contrast agent comprises one or more of iohexol and iodixanol, and said intermediate chemical compounds useful in the preparation of the non-ionic contrast agents are one or more of the compounds of formula II, III, IV, V and VI:

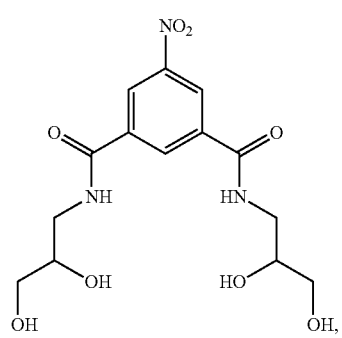

II

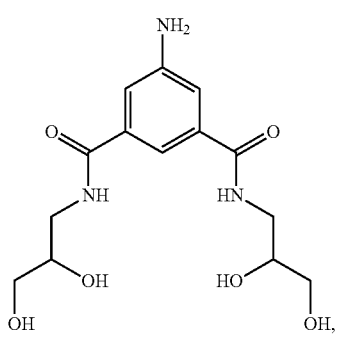

III

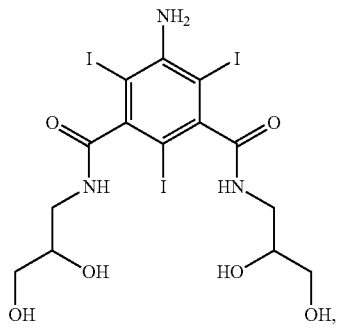

IV

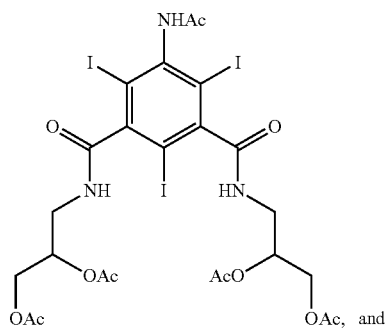

V

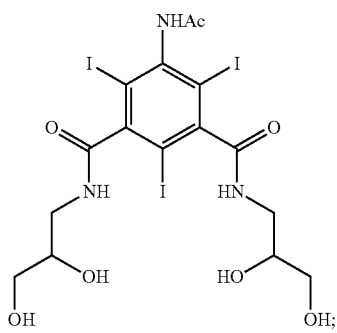

VI or wherein the non-ionic contrast agent is iopamidol, and said intermediate chemical compounds useful in the preparation of the non-ionic contrast agent are one or more of the compounds of formula VIII, IX, X, XI and XII:

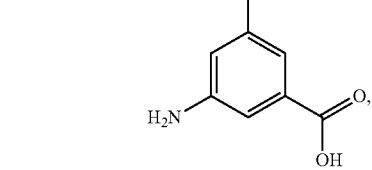

VII

-continued

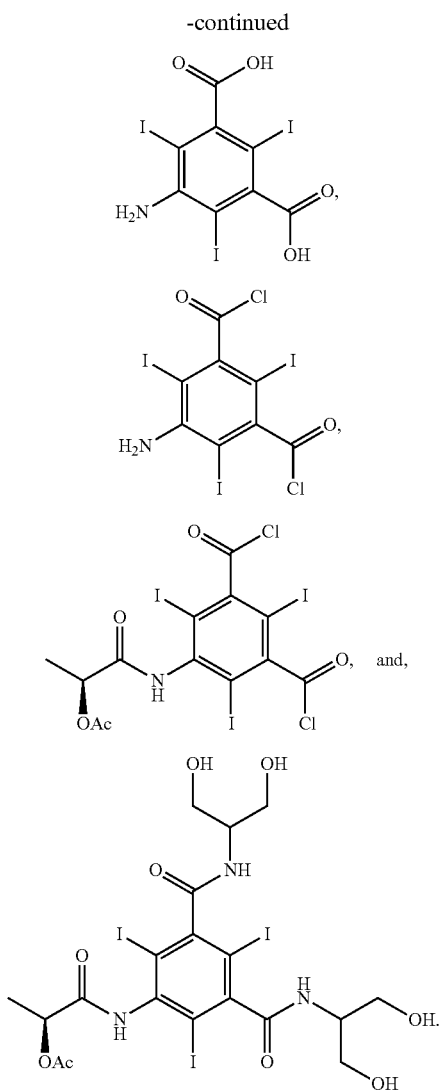

2. The process according to claim 1, wherein the one or more continuous flow reactors comprise a pipe reactor, a plug flow reactor, a tube reactor, a piston flow reactor, another commercially available continuous flow reactor, or a combination of two or more such reactors.

3. The process according to claim 1, wherein each reaction is carried out in a separate continuous flow reactor of the one or more continuous flow reactors.

4. The process according to claim 1, wherein an intermediate chemical compound resulting from the process is used to prepare a non-ionic contrast agent.

5. The process according to claim 1, wherein, in the (i) sequential set of steps,
   the product of the chemical reaction step i-a) is a first intermediate that is used as a reactant of the chemical reaction step i-b) to produce a second intermediate compound,
   this sequence being repeated in the same way for any subsequent reaction steps such that:
   the second intermediate compound being used as a reactant in the chemical reaction step i-c) to produce a third intermediate compound,
   the third intermediate compound being used as a reactant in the chemical reaction step i-d) to produce a fourth intermediate compound, and
   the fourth intermediate compound is used as a reactant in the chemical reaction step i-e) to produce a fifth intermediate compound,
   and wherein all of the sequential reaction steps are carried out consecutively without interruption.

6. The process according to claim 1, wherein the process is carried out without isolation or purification of any intermediate chemical compound, except if desired the final intermediate compound from the process.

7. The process according to claim 1, wherein the process further comprises one or more of the following:
   (i) one or more washing steps;
   (ii) one or more purification steps;
   (iii) one or more isolation steps; and
   (iv) the use of one or more solvents; and optionally, one or more solvent modification steps and/or solvent switching steps.

8. The process according to claim 1, further comprising controlling conditions within the one or more continuous flow reactors.

9. The process according to claim 8, wherein controlling the conditions comprises adjusting or altering one or more of the following:
   (i) the temperature within one or more of the one or more continuous flow reactors;
   (ii) the pressure within one or more of the one or more continuous flow reactors;
   (iii) the use of solvents or solvent systems within one or more continuous flow reactors;
   (iv) the flow rate(s) within one or more of the one or more continuous flow reactors; and,
   (v) the concentration of reactants within the feeds entering one or more of the one or more continuous flow reactors.

10. The process according to claim 8, wherein the flow rate of reagents through the one or more continuous flow reactors is controlled, altered or adjusted depending on the chemical reaction to be carried out.

11. The process according to claim 8, wherein the flow rates of reagents is different along one or more selected distances of the one or more continuous flow reactors, optionally wherein the one or more selected distances do not overlap.

12. The process according to claim 8, wherein the flow rate of reagents associated with a chemical reaction step affects the flow rate associated with the subsequent chemical reaction step.

13. The process according to claim 8, wherein reagents travel along a selected distance of the one or more continuous flow reactors at different flow rates.

14. The process according to claim 8, wherein the flow rates of reagents through the one or more continuous flow reactors is controlled, adjusted or altered using pumps, adjacent flow meters and control valves.

15. The process according to claim 1,
   wherein the nucleophilic acyl substitution of step ii-c) comprises one or more of the following:
      (a) substitution of an alcohol functional group for a halide;
      (b) substitution of a halide for an amine functional group; or,
      (c) amidation.

16. The process according to claim 1, wherein the nucleophilic acyl substitution reaction of step ii-c) is in the form of an amidation reaction wherein the yield of the amidation reaction is at least 95%.

17. The process according to claim 1, wherein the yield of the iodination reaction in either step i-c or step ii-b) is at least 85%.

18. The process according to claim 1, wherein the yield of the acylation reaction in either step i-d) or step ii-d) is at least 74%.

19. The process according to claim 1, wherein the yield of the selective hydrolysis reaction of step i-e) is at least 97%.

20. The process according to claim 1, wherein one of the two or more intermediate chemical compounds useful in the preparation of the one or more non-ionic contrast agents is the compound of formula VI or the compound of formula XII.

21. The process according to claim 1, wherein the one or more continuous flow reactors comprises one or more static mixing apparatuses.

22. The process according to claim 1, wherein the one or more continuous flow reactors comprise glass, silicon carbide, or stainless steel.

23. The process according to claim 1, wherein the process does not comprise the use of conventional stirred tank reactors (CSTRs) or other holding tanks.

24. The process according to claim 1, wherein one of the two or more intermediate compounds is compound VI.

25. The process according to claim 1, wherein one of the two or more intermediate compound is compound XII.

26. The process according to claim 1, wherein each reaction is carried out in a heterogeneous or homogeneous environment.

27. The process according to claim 1, wherein, in the (ii) sequential set of steps,
the product of the chemical reaction step ii-a) is a first intermediate that is used as a reactant of the chemical reaction step ii-b) to produce a second intermediate compound,
this sequence being repeated in the same way for any subsequent reaction steps such that:
the second intermediate compound being used as a reactant in the chemical reaction step ii-c) to produce a third intermediate compound, and
the third intermediate compound being used as a reactant in the chemical reaction step ii-d) to produce a fourth intermediate compound,
and wherein all of the sequential reaction steps are carried out consecutively without interruption.

* * * * *